US007704525B2

(12) United States Patent
Del Curto et al.

(10) Patent No.: US 7,704,525 B2
(45) Date of Patent: Apr. 27, 2010

(54) LIPID MICROPARTICLES BY CRYOGENIC MICRONIZATION

(75) Inventors: Maria Dorly Del Curto, San Quirico (IT); Daniela Chicco, Caravino (IT); Pierandrea Esposito, Ivrea (IT)

(73) Assignee: Ares Trading S.A., Aubonne (CH)

( * ) Notice: Subject to any disclaimer, the term of this patent is extended or adjusted under 35 U.S.C. 154(b) by 1861 days.

(21) Appl. No.: 10/451,676

(22) PCT Filed: Dec. 17, 2001

(86) PCT No.: PCT/EP01/14890

§ 371 (c)(1),
(2), (4) Date: Dec. 22, 2003

(87) PCT Pub. No.: WO02/051386

PCT Pub. Date: Jul. 4, 2002

(65) Prior Publication Data

US 2004/0091522 A1 May 13, 2004

(30) Foreign Application Priority Data

Dec. 27, 2000 (EP) ................... 00128556
Oct. 26, 2001 (EP) ................... 01125741

(51) Int. Cl.
  *A61K 9/127* (2006.01)
  *A61K 38/08* (2006.01)
  *A61K 38/21* (2006.01)
  *A61K 9/14* (2006.01)
(52) U.S. Cl. .................. 424/450; 424/85.4; 424/489; 514/15
(58) Field of Classification Search ............. 424/450, 424/489, 85; 514/2, 169, 15
  See application file for complete search history.

(56) References Cited

U.S. PATENT DOCUMENTS

| 4,483,847 | A |   | 11/1984 | Augart |
| 4,610,868 | A |   | 9/1986  | Fountain et al. |
| 4,837,381 | A |   | 6/1989  | Steber et al. |
| 5,192,741 | A |   | 3/1993  | Orsolini et al. |
| 5,340,588 | A | * | 8/1994  | Domb ......................... 424/450 |
| 5,430,021 | A |   | 7/1995  | Rudnic et al. |
| 5,470,947 | A | * | 11/1995 | Folkers et al. ............... 530/313 |
| 5,707,648 | A | * | 1/1998  | Yiv ............................ 424/450 |
| 6,551,619 | B1| * | 4/2003  | Penkler et al. ............. 424/489 |

FOREIGN PATENT DOCUMENTS

| DE | 198 19 273 A1 |   | 11/1999 |
| EP | 0 257 368     | * | 3/1988  |
| EP | 0 257 368 B1  |   | 3/1992  |
| EP | 0786251       | * | 7/1997  |

OTHER PUBLICATIONS

Morel et al., Incorporation in liopspheres of [D-Trp-6]LHRH, International Journal of Pharmaceutics 105 (1994) R1-R3.*
Morel, et al. Incorporation of Liospheres of [D-Trp-6]LHRH, International Journal of Pharmaceutics, 1994; 105, R1-R3.*
Allemann, et al., "Biodegradable Nanoparticles of Poly(lactic acid) and Poly(lactic-*co*-glycolic acid) for Parenteral Administration", Pharmaceutical Dosage Form: disperse systems $2^{nd}$ Ed. Marcel Decker Inc. 1998, 163-193.
Chen, et al., "Characterization of PLGA Microspheres for the Controlled Delivery of IL-1α for Tumor Immunotheraphy", Journal of Controlled Release. 1997, vol. 43, 261-272.
Fujimoto, et al., "Continued in vitro and in vivo Release of an Antitumor Drug from Albumin Microspheres", Experientia. 1983, vol. 39. 913-916.
Geze, et al., "Development of 5-iodo-2'-deoxyuridine Milling Process to Reduce Initial Burst Release from PLGA Microparticles", International Journal of Pharmaceutics. 1999, vol. 178, 257-268.
Golumbek, et al., "Controlled Release, Biodegradable Cytokine Depots: A New Approach in Cancer Vaccine Design", Cancer Research. Dec. 15, 1993, vol. 53, 5841-5844.
Jalil, Reza-UI, "Biodegradable Poly(lactic acid) and Poly(lactide-*co*-glycolide) Polymers in Sustained Drug Delivery", Drug Development and Industrial Pharmacy. 1990, vol. 16 No. 16, 2353-2367.
Jeyanthi, et al., "Preparation of Gelatin Microspheres of Bleomycin", International Journal of Pharmaceutics. 1987, vol. 35, 177-179.
Jones, et al., "In Vitro Release of Cytotoxic Agents from Ion Exchange Resins", Journal of Controlled Release. 1989, vol. 8, 251-257.
Liu, et al., "Controlled Release of Interleukin-2 for Tumour Immunotherapy Using Alginate/Chitosan Porous Microspheres", Journal of Controlled Release. 1997, vol. 43, 65-74. Mathiowitz, et al., "Biologically Erodable Microspheres as Potential Oral Drug Delivery Systems", Nature. Mar. 27, 1997, vol. 386, 410-414.
Muhlen, et al., "Solid Lipid Nanoparticles (SLN) for Controlled Drug Delivery—Drug Release and Release Mechanism", European Journal of Pharmaceutics and Biopharmaceutics. 1998, vol. 45, 149-155.
Muller, et al., "Solid Lipid Nanoparticles (SLN)—An Alternative Colloidal Carrier System for Controlled Drug Delivery", European Journal of Pharmaceutics and Biopharmaceutics. 1995, vol. 41 No. 1, 62-69.
Mumenthaler, et al., "Feasibility Study on Spray-Drying Protein Pharmaceuticals: Recombinant Human Growth Hormone and Tissue-Type Plasminogen Activator", Pharmaceutical Research. 1994, vol. 11 No. 1, 12-20.
Okada, et al., "Drug Delivery Using Biodegradable Microspheres", Journal of Controlled Release. 1994, vol. 28, 121-129.

(Continued)

*Primary Examiner*—Johann R Richter
*Assistant Examiner*—Andriae M Holt
(74) *Attorney, Agent, or Firm*—Browdy and Neimark, PLLC

(57) ABSTRACT

This invention relates to Lipid Microparticles consisting of lipids enriched in amphiphilic components, which promote the incorporation of peptides and/or protein, process for obtaining them as well as use thereof. A cryogenic micronization manufacturing process for their preparation is also disclosed.

25 Claims, 11 Drawing Sheets

OTHER PUBLICATIONS

Onishi, et al., "Chitosan-Drug Conjugate Microspheres: Preparation and Drug Release Properties of Microspheres Composed of the Conjugate of 2'- or 3'(4-Carboxy-butyreyl)-5-Fluorouridine with Chitosan", Drug Development and Industrial Pharmacy. 1996, vol. 22 No. 5, 457-463.

Parrot, Eugene, "Milling", The Theory and Practice of Industrial Pharmacy. 1986, 21-46.

Takenaga, Mitsuko, "Application of Lipid Microspheres for the Treatment of Cancer", Advanced Drug Delivery Reviews. 1996, vol. 20, 209-219.

Tsai, et al., "Preparation and in Vitro Evaluation of Polylactic acid-mitomycin C Microcapsules", J. Microencapsulation. 1986, vol. 3 No. 3, 181-193.

Tsung, et al., "Preparation and Stabilization of Heparin/Gelatin Complex Coacervate Microcapsules", Journal of Pharmaceutical Sciences. May 1997, vol. 86 No. 5, 603-607.

Willmott, et al., "Adriamycin-Loaded Albumin Microspheres: Preparation, in Vitro Distribution and Release in the Rat", Biopharmaceutics & Drug Disposition, 1985, vol. 6, 91-104.

* cited by examiner (a)

(b)

(a)

(b)

(see Fig. 6, previous page)
(c)
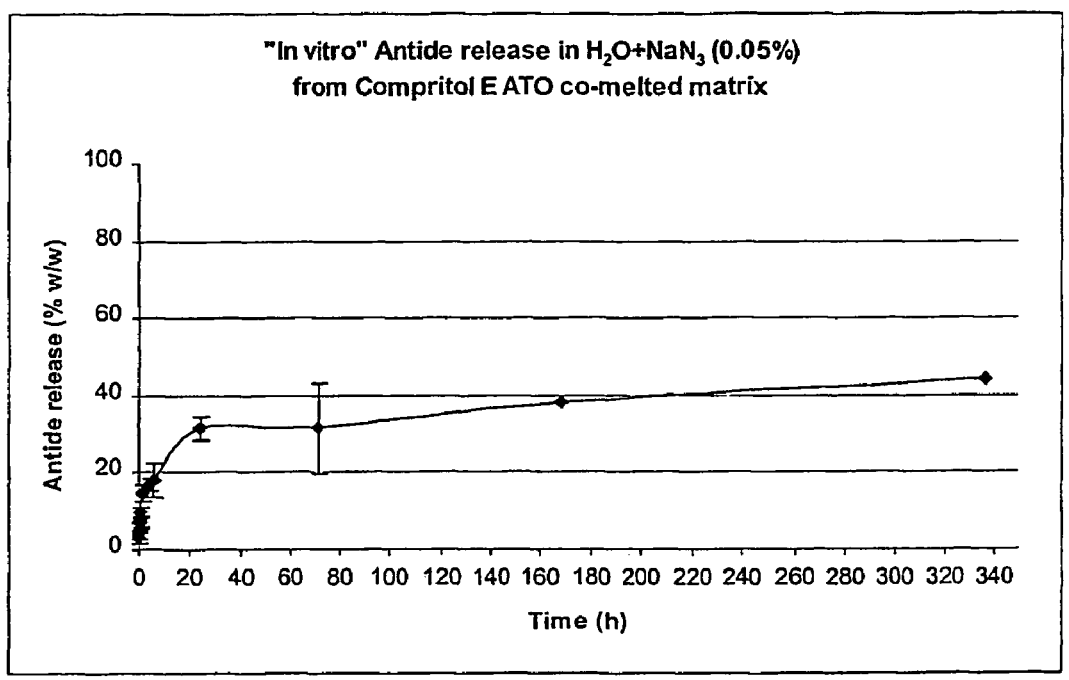
(d)
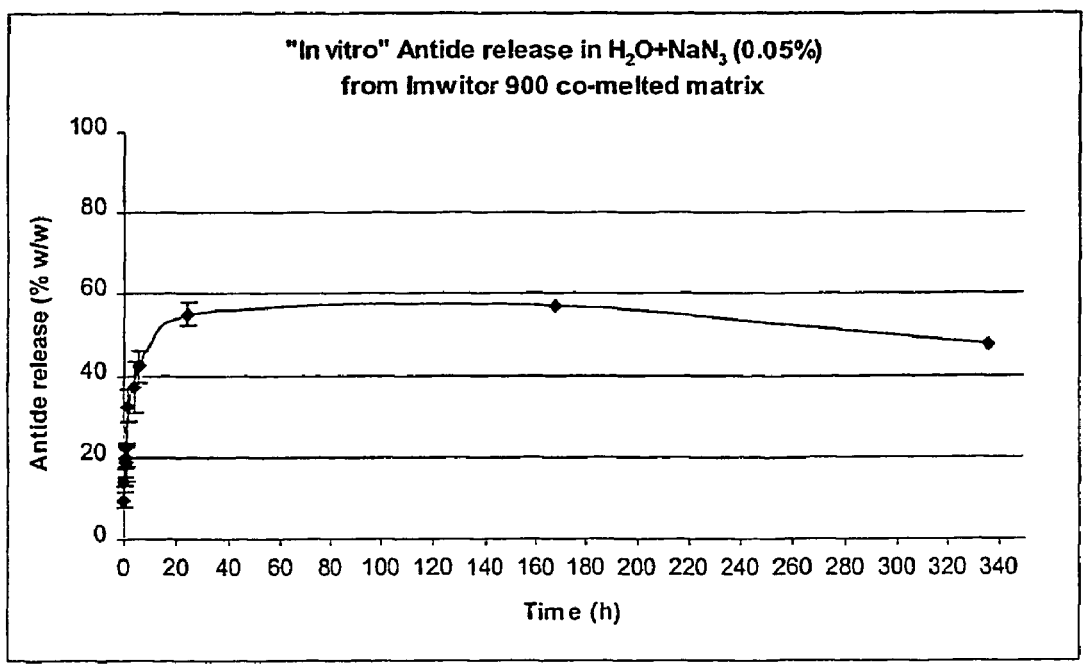

LIPID MICROPARTICLES BY CRYOGENIC MICRONIZATION

This application is a national stage application for PCT/EP01/14890 filed under 35 U.S.C. 371, filed Dec. 17, 2001.

FIELD OF THE INVENTION

This invention relates to lipid microparticles consisting of lipids enriched in amphiphilic components, which promote the incorporation of peptides and/or proteins, process for obtaining them as well as use thereof. A cryogenic micronization manufacturing process for their preparation is also disclosed.

BACKGROUND OF THE INVENTION

Microspheres are an example of a drug delivery system that has been evaluated extensively in several therapeutic fields. They are essentially solid particles with 1 to 500 µm in diameter which can both target their drug cargo by physical trapping in blood vessels (chemoembolisation) and sustain the action of a therapeutic agent through controlled release. Microspheres can be made from a broad range of materials, including proteins, polysaccharides, polyesters and lipids by a variety of different techniques (emulsification, heat stabilisation, coacervation and phase inversion technology). Microspheres are monolithic structures, solid throughout, and distinguishable from more fluid and flexible vesicular systems such as liposomes. They are normally 1-500 µm in diameter and fall between granules (>100 µm) and microparticles (<1 µm). They distinguish from microcapsules for their internal structure, being a homogeneous matrix rather than a vesicular form. Microspheres can be produced from a number of different biocompatible biodegradable materials such as protein (albumin and gelatin) (*Biopharm. Drug. Dispos.* (1985) 6 pp. 91-104 and *Intern. J. Pharm.* (1987) 35 pp. 177-179), polyesters (glycolide and lactide) (*J. Microencap.* (1986) 3 pp. 181-193 and *Drug Dev. Ind. Pharm.* (1990) 16 pp. 2353-2367), polysaccharides (starch, ethyl cellulose, alginate and chitosan) (*Drug Dev. Ind. Pharm.* (1996) 22 pp. 457-463 and *J. Contrl. Rel.* (1997) 43 pp. 65-74), ion exchange resins (*J. Contrl. Rel.* (1989) 8 pp. 251-257) and lipids (*Adv. Drug Deliv. Rev.* (1996) 20 pp. 209-219).

Until now, many approaches have been developed to form microspheres whilst simultaneously encapsulating the drug, including such diverse techniques as:

chemical stabilisation (*Biopharm. Drug. Dispos.* (1985) 6 pp. 91-104);
heat stabilisation (*Experientia* (1983) 39 pp. 913-916);
multiple emulsion solvent evaporation (*J. Contr. Rel.* (1994) 28 pp. 121-129);
multiple emulsion solvent extraction (*J. Contr. Rel.* (1997) 43 pp. 261-272);
coacervation (*Cancer Res.* (1993) 53 pp. 5841-5844);
phase inversion nanoencapsulation (PIN) (*Nature* (1997) 386 pp. 410-414);
spray drying (*Pharm. Sci.* (1997) 86 pp. 603-607).

Occasionally a drug is added to or complexed onto microspheres after particle formation. Selection of the matrix material and method of preparation are critical in defining overall performance.

The choice will depend on several factors:
size of microspheres required;
inherent properties of the drug, for example, aqueous solubility and stability;
surface characteristics of particles, such as permeability and charge;
degree of biodegradability and biocompatibility;
drug release profile desired.

The rate with which the drug is released from microspheres is dependent on three main factors:
solubility of the encapsulated drug and diffusion processes;
rate of particle erosion and biodegradation;
interaction between the drug and the particle matrix leading to immobilisation.

Polymeric microparticle are usually prepared by techniques such as single/double emulsion-solvent evaporation, coacervation and spray drying.

These techniques however show some drawbacks: in the solvent evaporation method, high quantity of chlorinated organic solvents are normally used and controlled operative conditions can be rarely achieved; moreover in the case of peptide and proteins the solvents used can denature the structure and lead to a loss of potency. In the O/W single and double emulsion it has been also reported that the accumulation of amphiphilic molecules (i.e. proteins) at organic/aqueous interface layer could cause drug aggregation and precipitation. (*Pharmaceuticals Dosage Forms: Disperse systems* $2^{nd}$ Edition. Marcel Dekker Inc. (1998) pp. 163-193).

Spray-drying is a technique in which the polymer and the drug, solubilized or suspended in a medium, are atomized through a nozzle in a chamber where the solvent is forced to evaporate by the effect of a relatively high temperature and the microparticles are collected in powder form at the end of the process. By such evaporation technique the matrices obtained are normally quite porous, leading to a poor drug encapsulation within the matrix resulting in a fast release and in a large initial burst effect. Moreover the air/liquid interface formed during the preparation enhance molecule aggregation (especially for proteins) at the surface. (Mumenthaler M. et al. *Pharm. Res.* 11 (1994), No. 1).

Therefore the cryogenic micronization can be envisioned as alternative manufacturing method for obtaining microparticles of lipid material, that could lead to remarkable advantages, both in terms of peptide/protein stability and in terms of reducing the burst effect. Moreover, drug release profile can be modulated by obtaining a defined physical state of the lipid, having said lipids various crystalline states (such as polymorphic states).

In the examined prior art, some examples of lipid microparticles have already been described for industrial application in the field of drug release. W. Steber et al. (American Cyanamid Corporation, EP 257368) describe a microsphere composition, containing from 30 to 95% of fats or waxes and about 2 to 70% of a biologically active substance, where the lipid component contains a glyceril tristerate content from 55 to 79%. M. W. Fountain et al. from The Liposome Company, U.S. Pat. No. 4,610,868) claim lipid matrix carriers comprising a hydrophobic compound, an amphipathic compound and a bioactive agent, combined in the form of globular structure, having a diameter from 500 nm to 100 µm. Said carrier is obtained by emulsifying the components and injecting the emulsion into an organic solvent. H. Augart (Warner Lambert Company, U.S. Pat. No. 4,483,847) described a composition for the delivery of drugs, comprising both high and low melting lipids, that after melting, mixing and cooling are granulated for the production of tablets. P. Orsolini et al., (Debiopharm, U.S. Pat. No. 5,192,741) describe a process comprising a cryogenic grinding step, for preparing a pharmaceutical composition containing polylactide, copolymer of lactic and glycolic acid and peptides. Microparticles are obtained by dissolving/dispersing said polymers and the bioactive agent into an organic solvent, removing the solvent while shaping the solid residue.

It is therefore an objective of the present invention to provide lipid microparticles with sustained release and especially a low "burst effect".

DESCRIPTION OF THE INVENTION

In particular, the main object of the invention is to provide a new type of lipid microparticles comprising a drug and a lipid matrix characterized in that said drug is a peptide or a protein and said lipid matrix has a monoglyceride content which is at least 70% w/w, the percentage being based on the weight of the lipid matrix.

To obtain an enhanced incorporation of said peptides and/or proteins in the lipid matrix, several lipids with different hydrophilic/hydrophobic characteristics and chemical compositions have been screened, such as for example tri-o di- and mono-glycerides, PEG- or PPG-glycerides, saccharide-glycerides, fatty acids and mixture thereof.

Surprisingly, it has been observed that the maximum peptide and/or protein loading can be obtained by using a lipid matrix containing a high monoglyceride content, which confers amphiphilic properties to the lipid microparticles. It has been found that the monoglyceride content of said lipid matrix amount should be at least 70% w/w, particularly from 75 to 99% w/w. Therefore, according to the present invention, any of the above-mentioned lipids or any mixture of one or more of them may be used, provided that the total amount of monoglyceride content is at least 70%, as explained above.

Lipid microparticles of the invention may also include pharmaceutically acceptable excipients, such as polymers having bioadhesive or absorption enhancing properties and selected from the group comprising or consisting of acrylic polymers (Carbopol®, Polycarbophil, Noveon®), medium chain fatty acids and polyethylene glycols. Preferred excipients are the above-mentioned acrylic polymers.

According to a preferred embodiment of the invention the total lipid content of the microparticles is at least 90% w/w, more preferably 95% w/w.

Typically any therapeutically effective peptide or protein may be incorporated into the lipid microparticles of the invention. Most of the therapeutically useful proteins may be grouped into 3 classes:

regulatory factors including hormones, cytokines, lymphokines, chemokines, their receptors and other regulatory factors of cellular growth and metabolism comprising enzymes;

blood products including serum-derived blood factors and enzymatic fibrinogen activators;

monoclonal antibodies.

According to an embodiment of the invention, suitable proteins or peptides as above-mentioned include, but are not limited to, the following examples: AAT, UK, PUK, streptokinase, tPA, SOD, insulin, GH, GRF, ANF, GnRH, LHRH analogs, erythropoietin, granulocyte CSF, granulocyte macrophage CSF, Interleukin-1, Interleukin-2, Interleukin-3/multipotential CSF, Interleukin-4, Interleukin-5 (or Eosinophil-CSF), Interleukin-6, Interleukin-7, Interleukin-8, Interleukin-9, Interleukin-10, Interleukin-11, interferon-α, interferon-β, interferon-γ, Leukemia inhibitory factor Macrophage CSF, TNF, Stem cell factor as well as receptors thereof.

According to a preferred embodiment of the invention, said protein or peptide is selected from the group consisting of Interleukin-6, Interferon-α, Interferon-β, Interferon-γ, GnRH, LHRH analogs, GH, GRF, gonadotropins (like FSH, LH and hCG) and TNF receptors or soluble fragments thereof.

More preferably the peptide is selected from the group consisting of LHRH analogs, and more particularly a decapeptide acting as LHRH antagonist.

In a particularly preferred embodiment of the present invention, a non-limiting list of said peptides includes the following compounds:

Abarelix (disclosed in WO 9640757), acts as LHRH antagonist and is defined by the formula hereinafter:

D-Alaninamide, N-acetyl-3-(2-naphthalenyl)-D-Ala-4-Cl-D-Phe-3-(3-pyridinyl)-D-Ala-L-Ser-N-methyl-L-Tyr-D-Asn-L-Leu-N-6-(1-methylethyl)-L-Lys-L-Pro.

Antarelix (disclosed in WO 9219651), acts as LHRH antagonist and is defined by the following formula:

D-Alaninamide, N-acetyl-3-(2-naphthalenyl)-D-Ala-4-Cl-D-Phe-3-(3-pyridinyl)-D-Ala-L-Ser-L-Tyr-N-6-(aminocarbonyl)-D-Lys-L-Leu-N-6-(1-methylethyl)-L-Lys-L-Pro.

Azaline B (disclosed in U.S. Pat. No. 5,296,468), acts as GnRH antagonist and is defined by the following formula:

D-Alaninamide, N-acetyl-3-(2-naphthalenyl)-D-Ala-4-Cl-D-Phe-3-(3-pyridinyl)-D-Ala-L-Ser-4-[(5-amino-1H-1,2,4-triazol-3-yl)amino]-L-Phe-4-[(5-amino-1H-1,2,4-triazol-3-yl)amino]-D-Phe-L-Leu-N-6-(1-methylethyl)-L-Lys-L-Pro.

Ganirelix (disclosed in EP 277829), acts as LHRH antagonist and is defined by the following formula:

D-Alaninamide, N-acetyl-3-(2-naphthalenyl)-D-Ala-4-Cl-D-Phe-3-(3-pyridinyl)-D-Ala-L-Ser-L-Tyr-N6 [bis(ethylamino)methylene]-D-Lys-L-Leu-N-6-[bis(ethylamino)methylene]-L-Lys-L-Pro.

In a more preferred embodiment of the present invention, said peptide acting as LHRH antagonist is a specific decapeptide named Antide. This decapeptide (N—Ac-D-2-NaI, D-pClPhe, D-3-Pal, NicLys, D-NicLys, Ilys, D-Ala, $NH_2$) has an impressive antiovulatory activity as well as LHRH antagonistic properties and has already been described (EP 377665 and U.S. Pat. No. 5,470,947) as acting directly on the hormonal metabolism in a woman.

Another particular preferred peptide acting as LHRH antagonist is another decapeptide named Cetrotide, (whose INN is Cetrorelix disclosed EP 299402) having the following formula: D-Alaninamide, N-acetyl-3-(2-naphthalenyl)-D-Ala-4-Cl-D-Phe-3-(3-pyridinyl)-D-Ala-L-Ser-L-Tyr-N5-(aminocarbonyl)-D-ornithyl-L-Leu-L-Arg-L-Pro.

Hence, it is herein reported that the peptide- or protein-loaded lipid microparticles are indeed suitable for being used as a medicament, for the preparation of a pharmaceutical composition. In the preferred case, where the peptide is a decapeptide acting as LHRH antagonist, the pharmaceutical composition will be useful for the modulation of the hormonal metabolism in a mammal or for the treatment or prevention of disorders associated with abnormal activity of the hormonal metabolism in a woman. More specifically, for the treatment or prevention of disorders associated with abnormal activity of the LHRH pathway. In this specific case, peptide-loaded lipid microparticles are useful for the treatment of hormonal diseases, pathological states or contraceptive actions in which antagonizing of LHRH play a major role, such as contraceptive agent for inhibiting the ovulation in mammal or inhibiting the growth of hormone-dependent tumors, or the testosterone production in a mammal. Peptide-loaded lipid microparticles could be employed alone or in combination with other pharmaceutical agents.

When employed as pharmaceuticals, peptide- or protein-loaded lipid microparticles of the present invention are typically administered in the form of a pharmaceutical dosage form. Hence, pharmaceutical compositions comprising peptide- or protein-loaded lipid microparticles and pharmaceutically acceptable excipients, such as diluents, antioxidizing agents, surfactants, co-surfactants, viscosizing agents, antimicrobials, cryo-protectants are also in the scope of the present invention. Such composition can be prepared in a manner well known in the pharmaceutical art. Generally, the peptide- or protein-loaded lipid microparticles of the present invention are administered in a therapeutically effective amount. The amount actually administered will typically be determined by a physician, in the light of the relevant circumstances, including the condition to be treated, the chosen route of administration, the age, weight, and response of the individual patient, the severity of the patient's symptoms, and the like.

The pharmaceutical compositions of these inventions can be administered by a variety of routes including oral, intravenous, subcutaneous, intramuscular, intraarterial, intraperitoneal, dermal, sublingual, rectal, buccal, vaginal, nasal or pulmonary routes. The subcutaneous route is the preferred route of administration according to the invention.

Depending on the intended route of delivery, the compounds can be formulated either as liquid or as solid forms. The compositions for oral administration can take the form of bulk liquid solutions or suspensions, or bulk powders.

Liquid forms suitable for oral administration may include a suitable aqueous or non-aqueous vehicles together with buffers, suspending and dispensing agents, colorants, flavors and the like.

Solid forms may include, for example, any of the following ingredients, or compounds of a similar nature: a binder such as microcrystalline cellulose, gum tragacanth or gelatine; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable carriers known in the art.

A further object of the present invention is a process for preparing the lipid microparticles loaded with a peptide or a protein, which have been set out above. According to a preferred method of production, peptide- or protein-loaded lipid microparticles of the present invention can be prepared by a new cryogenic micronization manufacturing process for lipid microparticles comprising a biologically active substance, preferably a peptide and use thereof as pharmaceutical composition.

Said new process can be viewed as a new way to obtain a suitable delivery system comprising peptide, particularly decapeptide, and characterized by its sustained release (*Eur. J. Pharm. Biopharm.* 41 (1995) (1) pp. 62-69 and *Eur. J. Pharm. Biopharmn.* 45 (1998) pp. 149-155).

According to an embodiment of the present invention, lipid microparticles manufacturing process comprises the steps of:
 loading the lipid with a drug solubilized in a solvent;
 eliminating the solvent;
 cooling the drug-loaded lipid matrix;
 pre-reduction by grinding of so-obtained material;
 cryogenic micronization performed after cooling, milling and sieving.

According to another embodiment of the invention, lipid microparticles manufacturing process comprises the steps of:
 loading said peptide into the molten lipid;
 cooling of the drug-loaded lipid matrix;
 pre-reduction by grinding of so-obtained material;
 cryogenic micronization performed after cooling, milling and sieving.

Regarding to the grinding process mentioned before the last step, said grinding is a basic method for particle size reduction of powders during the pharmaceutical solid dosage forms production (Lachman L. and Lieberman H., *Lea & Febiger* (1986), pp. 2146). However with the latest equipment improvements (high-speed mills, micronizers, in line classifiers) it is now possible to achieve by milling micron and sub-micron range particles with controlled dimensions and size distribution.

Quite surprisingly, grinding is rarely reported as lipid microparticle manufacturing process. When the microparticle preparation involves the use of polymers, the impact/friction forces that arise during grinding are not efficient as a mean for particle size reduction. This is due to the structure of the most common polymers used, which show rubbery characteristics (glass transition events) that decrease the efficiency of particle size reduction by grinding methods (Geze et al. *Int. J. Pharm.* (1999) pp. 257-268 and Domb et al. *Handbook of Biodegradable Polymers Harwood Academic Publishers* (1997) pp. 3-29).

On the contrary, when dealing with lipids, due to their different physical structure, which is characterized by a certain degree of crystallinity, the application of impact/friction forces, and therefore grinding technique can be successfully used.

Therefore micronization can be envisioned as alternative manufacturing method for obtaining microparticles of lipid material, that could lead to remarkable advantages, especially when peptides/proteins have to be incorporated.

Moreover, another advantage of the micronization process is the possibility of operating in cryogenic conditions ("cryogenic micronization"), which can be useful when dealing with thermosensitive drugs (i.e. peptides, proteins), materials with low glass transition temperature or melting point, such as lipid blends or composite materials with physico-chemical properties closer to polymeric structure.

According to a more preferred method of production, peptide-loaded lipid microparticles of the present invention are prepared according to the solvent stripping technique:
 loading the lipid with the peptide co-solubilized in the organic solvent;
 eliminating the solvent;
 cooling the drug-loaded lipid matrix;
 size pre-reduction by grinding of so-obtained matrix;
 cryogenic micronization;
 milling and sieving of the so-obtained microparticles.

According to another preferred embodiment of the invention, solvent used is selected from the group consisting of water, ethanol, propanol, benzyl alcohol, isopropanol, or a mixture thereof, particularly a mixture of ethanol and benzyl alcohol and more particularly benzyl alcohol.

In a preferred embodiment of the invention, solvent evaporation is carried out at a temperature comprised of between 30° C. and 90° C., preferably of between 40° C. and 80° C. and more preferably of between 55° C. and 75° C.

According to a preferred method of production, peptide-loaded lipid microparticles are prepared according to the co-melting technique and comprising the steps hereinafter:
- loading the peptide into the molten lipid;
- cooling the drug-loaded lipid matrix;
- size pre-reduction by grinding of so-obtained matrix;
- cryogenic micronization;
- milling and sieving the so-obtained microparticles.

Pre-reduction step of the lipid matrix is performed by hammer-milling or knife-milling or oscillating-milling.

In the cryogenic micronization step, cooling is performed by insufflating liquid nitrogen at a temperature comprised in the range from −196° C. to 0° C., particularly from −80° C. to −20° C. and more particularly from −50° C. to −30° C., before the drug loaded lipid matrix be micronized. So obtained microparticles size is comprised in a range from 1 μm to 500 μm, particularly from 1 μm to 300 μm, more particularly from 1 to 100 μm and especially from 5 to 50 μm.

Regarding to the sieving step, this operation is depending on particle size requirements and on the type of mill used, the particle size of the product obtained by micronization can already be suitable for some applications and therefore sieving is not necessary.

A common problem with drug release from microspheres is known as the "burst effect" where a large percentage (30-70%) of the total payload can be released from particles over a short period of time (1 h or less). This is believed to be due to the rapid release of the drug that is near to the surface of the microspheres or to highly porous matrices or to rapid erosion of the polymeric material.

Quite surprisingly, it has been observed that lipid microparticles loaded with Antide and obtained by the process according to the invention showed a sustained release in-vivo for at least 1 month, with an initial burst effect that could be controlled and modulated (down to 10% of drug released in 24 hours), both by manufacturing operative conditions (i.e. incorporation method) and physico-chemical characteristics of the materials (i.e. glyceride composition), as shown in FIG. 5. Surprisingly, both these factors affect the structural arrangement of the lipid matrix itself and the drug loaded matrix, which results in the possibility of controlling drug release and adjusting the burst to the desired values. Furthermore it has been observed that a high monoglyceride content of the lipid phase gives a lower initial "burst effect" (see FIG. 10).

This paragraph provides abbreviations and definitions of the various biological and analytical terms as well as abbreviations used throughout this patent application and are intended to apply uniformly throughout the specification and claims unless and otherwise expressly set out.

"amphiphilic" refers to a compound having affinity for two different environments—for example a molecule with hydrophilic (polar) and lipophilic (non-polar) regions. Detergents are classic examples.

"AAT" refers to α-1-antitrypsin

"ANF" refers to Atrial Natriuretic Factor

"Antide", for which Iturelix is the proposed INN, refers to the following decapeptide:

N—Ac-D-2-NaI, D-pCiPhe, D-3-Pal, Ser, NicLys, D-NicLys, Leu, Ilys, Pro, D-Ala, NH$_2$.

wherein:

"Burst effect" refers to a common problem with drug release from microspheres where a large percentage (50-70%) of the total payload can be released from particles over a short period of time (1 h). This is due to the rapid release of material that is not correctly embedded into the microspheres.

"Co-melting technique": technique allowing to load a drug into a given melted material in liquid phase "2-NaI" refers to 3-(2-naphtyl)alanine "Ilys" refers to N-isopropyllysine "NicLys" refers to N-nicotynoyllysine "3-Pal" refers to 3-(3-pyridyl)alanine "DMPC" refers to DiMyristoyl Phosphatidyl Choline "DMPG" refers to DiMyristoyl Phosphatidyl Glycerol "FACTOR VIII" refers to a glycoprotein containing 2331 amino acids "FSH" refers to Follicular Stimulating Hormone.

"GH" refers to Growth Hormone

"Glycerides" is intended to mean glycerol esters of $C_4$-$C_{30}$ saturated or unsaturated fatty acids "GRF" refers to Growth hormone Releasing Factor "GnRH" refers to Gonadotropine Releasing Hormone "HPH" refers to High Pressure Homogenization "LD" refers to Laser Diffractometry "LHRH" refers to Luteinizing Hormone Releasing Hormone "Lipid", according to the present invention refers to a substance that is poorly soluble in water but is soluble in organic solvents. According to the present invention, lipids include fatty acids, mono-di- and tri-glycerides, phospholipids, PEG-glycerides, saccharide-glycerides or waxes and any mixture thereof. According to the invention, the lipid matrix is always intended to be pharmaceutically acceptable.

"LM" refers to Lipid Microparticles.

"Microparticles" refers to particles whose average diameter is comprised in a range between 3 μm and 500 μm.

"Monoglycerides" refers to compounds obtained applying esterification by fatty acid of one of the glycerol alcohol functions such as shown hereinafter:

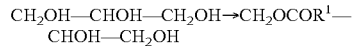

Glycerol Monoglyceride wherein $R^1$ is a $C_4$-$C_{30}$ saturated or unsaturated hydrocarbon chain;

or by partial hydrolysis of triglycerides.

"NMR" refers to Nuclear Magnetic Resonance.

"PCS" refers to Photon Correlation Spectroscopy.

"PEG" refers to Polyethyleneglycol.

"Peptide" means a polyamide back-bone containing tetrahedral carbon atoms between amide groups. The peptide chain is obtained from condensation of amino acids: the amino group of one joins the carboxyl group of the next, forming a peptide bond.

"Pharmaceutically acceptable" is meant to encompass any substance, which does not interfere with the effectiveness of the biological activity of the active ingredient and that is not toxic to the host to which is administered.

"Proteins" refers to a molecule comprising a polypeptide amino add sequence. The main distinction between peptides and proteins is one of size. According to the present invention peptides contain not more than 100 amino acids, whereas proteins contain more than 100 amino acids.

"PUK" refers to Pro-urokinase

"Saccharide" refers to an aldehyde group or a ketone group having at least two hydroxyl groups, said saccharide adopting several forms: monomer form (monosaccharide), dimer form (disaccharide), trimer form (trisaccharide), oligomer (oligosaccharide) and polymer (polysaccaharide).

"SOD" refers to Superoxide Dismutase

"Solvent-stripping technique": technique allowing to load the drug (i.e peptide), solubilized in a solvent, into a carrier material (i.e. lipid) melted or solubilized in a solvent "Therapeutically effective amount" refers to an amount that is sufficient to affect the course and the severity of the diseases described above, leading to the reduction or remission of such pathology. The effective amount will depend on the route of administration and the condition of the patient.

"TNF" refers to Tumor Necrosis Factor

"tPA" refers to Tissue Plasminogen Activator

"UK" refers to urokinase

"w/w" refers to weight/weight.

The present invention is illustrated by some examples, that demonstrate the possibility of using different processes with different lipids to achieve different drug loadings and to obtain different release rates, but are not intended to limit in any way the scope of the invention. The Examples will make reference to the following Figures.

Assessment of the in vitro bioactivity of Antide incorporated in different lipid matrices.

Formulation A=2% Antide-loaded Compritol E ATO co-melted matrix.

Formulation B=2% Antide-loaded Compritol E ATO stripped matrix.

FIG. 3:

LD frequency (bell-shaped) and volume undersize (sigma-shaped) curves of 2% Antide-loaded Imwitor 900 co-melted lipid microparticles (a), and 2% Antide-loaded stripped Compritol E ATO lipid microparticles (b).

FIG. 4:

Solid State $^{13}$C-NMR spectra obtained on bulk drug (B) and stripped Imwitor 900 matrix containing 20% Antide (A).

FIG. 5:

Solid State $^{13}$C-NMR spectra obtained on bulk drug (B) and co-melted Imwitor 900 matrix containing 10% Antide (A).

FIG. 6:

Antide cumulative release profiles from different 2% (w/w) Antide loaded lipid matrices.

FIG. 7:

Antide release from Compritol E ATO stripped matrices at different drug loading.

FIG. 8:

Antide plasma concentration/time profiles after in vivo s.c. administration in rats of 2% Antide loaded lipid matrices;

FIG. 9:

This Figure relates to testosterone plasma levels after s.c. administration in rats of the four lipid microparticles formulations mentioned in the previous figure description.

Formulation 1: Antide (2% w/w)-Compritol E ATO (stripped)

Formulation 2: Antide (2% w/w)-Imwitor 900 (stripped)

Formulation 3: Antide (2% w/w)-Compritol E ATO (co-melted)

Formulation 4: Antide (2% w/w)-Imwitor 900 (co-melted)

FIG. 10:

This Figure shows the release profiles in water of LM-Antide2%-Compritol C888 (batch 93) and LM-Antide 2%-Compritol E ATO (batch 106). Compritol 888 contains a monoglyceride content between 12 and 18% whereas Compritol E ATO has a monoglyceride of about 80%.

EXAMPLES

Figure 1:
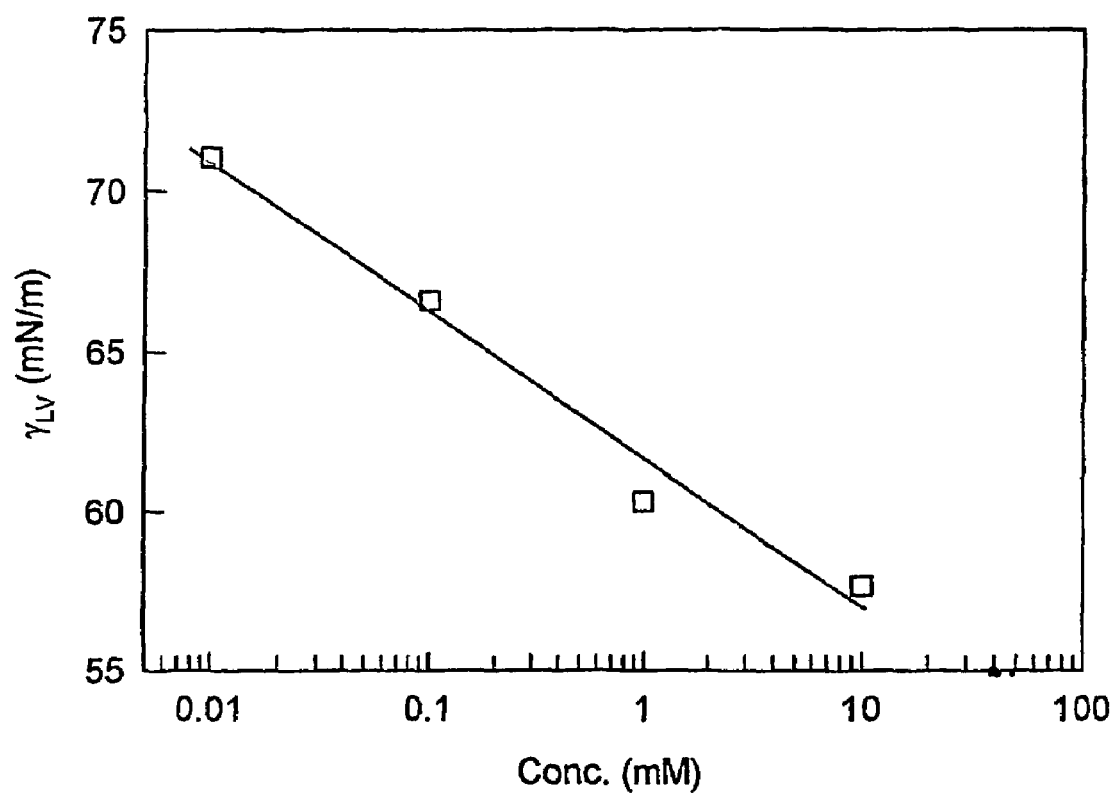
FIG. 1: This figure relates to surface tension of Antide water solutions at different drug concentrations.

The peptide used in the Examples reported here below is Antide. This peptide has amphiphilic characteristics, as demonstrated by the following data:

Surface tension analysis: surface tension measurement was carried out using a Kruss tensiometer (drop shape analysis system) on Antide water solutions at different drug concentrations, namely 0.01, 0.1, 1.0, 10 mM. The results are shown in FIG. 1.

Partition coefficient: it was determined using octanol as organic phase and water as hydrophilic phase. The two phases were first saturated with each other for 24 hours at room temperature. Antide was then dissolved in the water phase at a concentration well below saturation. An equal volume of organic phase was subsequently added to the water phase and the mixture was kept under stirring for 24 hours at room temperature. Antide concentration in the two phases was determined by RP-HPLC and the partition coefficient was obtained from the ratio between the drug concentration in organic and water phase.

The resulting octanol/water coefficient was $8.56 \cdot 10^{-2}$

The results of Antide semi-quantitative solubility evaluation in some lipids, along with the lipid monoglyceride content are shown in Table 1.

Materials and Equipment:

Antide bulk, Bachem.

Imwitor 900 (Glyceryl monostearate), Condea Chemie-DE.

Compritol E ATO (Glyceryl monobehenate), Gattefossé-FR.

Compritol 888 ATO (Glyceryl behenate), Gattefossé-FR.

Imwitor 312 (Monoglyceride of lauric acid), Condea Chemie-DE.

Imwitor 928 (Glyceryl mono-/di-cocoate), Condea Chemie-DE.

Geleol (Glyceryl mono-palmitate/stearate), Gattefossé-FR.

Compritol HD 5 ATO (Glyceryl/polyethylene glycol behenate), Gattefossé-FR.

Superpolystate (Polyethylene glycol stearate), Gattefossé-FR.

Precirol ATO 5 (Glyceryl mono-/di-/tri-palmitate/stearate), Gattefossé-FR.

Witepsol E 85 (Tri-glycerides of $C_{10}$-$C_{18}$ saturated fatty acids), Massa Witepsol Softisan 142 (Hydrogenated coco-glycerides), Condea Chemie-DE.

Gelot 64 (Glyceryl/polyethylene glycol palmitate/stearate), Gattefossé-FR.

Monosteol (Palmitate/stearate of propylene glycol), Gattefossé-FR.

Gelucire 44/14 (Defined blend of mono-/di-/tri-esters of lauric acid with glycerol and polyethylene glycol), Gattefossé-FR.

Gelucire 50/13 (Defined blend of mono-/di-/tri-esters of stearic acid with glycerol and polyethylene glycol), Gattefossé-FR.

Cetil alcohol, Sigma

Ethanol, Merck-D

Benzyl Alcohol, Sigma-USA

IFN-β liquid formulation (REBIF®—Serono)

Vacuum oven OVAO31.XX1.5, Sanyo Gallenkamp; vacuum pump LA.12, D.V.P. Vacuum

Technology

Autosieving system, Retsch AS 200

Laser Difractomer Mastersizer Microplus MAF 5001, Malvern

Waters HPLC system: 2690 Separation Module; RP column, Jupiter 5 µm C18 (250×4.6 mm, 5 µm); 2487 Dual λ Absorbance Detector Cryogenic mill-Apex, Mod. MPX3: customized as described below The cryogenic mill used for these studies is a conventional hammer mill equipped with a nozzle suitable for the introduction of a cooling gas (i.e. liquid $N_2$) in the chamber. After preliminary grinding trials, a customization was performed on the mill, in order to make it more suitable for our needs. The following modifications were made:

- introduction of a thermometric probe for temperature measurement in the milling chamber;
- sealing of the bottom screen with a blind blade to avoid powder loss from the milling chamber;
- installation of a piston for powder introduction into the milling chamber; and
- connection to liquid $N_2$ tank by a thermo-isolated pipe.

Example 1

2% Drug-Loaded Lipid Microparticles, Prepared by Solvent-Stripping Technique Using Compritol E ATO as Lipid Matrix The peptide (Antide) and the lipid (Compritol E ATO) in a w/w ratio of 2:98 were solubilized at 85° C. in the organic solvent (mixture of Benzyl alcohol and Ethanol, 1:5) under stirring. The solvent was evaporated under vacuum at 80° C. The lipid matrix was then cooled down to room temperature, pre-ground and micronized under cryogenic conditions. Finally the microspheres were sifted at 125 µm and collected.

Example 2

2% Drug-Loaded Lipid Microparticles, Prepared by Solvent-Stripping Technique Using Imwitor 900 as Lipid Matrix The peptide (Antide) and the lipid (Imwitor 900) in a w/w ratio of 2:98 were solubilized at 80° C. in the organic solvent (mixture of Benzyl alcohol and Ethanol, 1:2) under stirring. The solvent was evaporated under vacuum at 60° C. The lipid matrix was then cooled down to room temperature, pre-ground and micronized under cryogenic conditions. Finally the microspheres were sifted at 125 µm and collected.

Example 3

2% Drug-Loaded Lipid Microparticles, Prepared by Co-Melting Technique Using Compritol E ATO as Lipid Matrix The peptide (Antide) was incorporated into the molten lipid (Compritol E ATO) under stirring (the w/w drug-lipid ratio was 2:98). The lipid matrix was then cooled down in an ice-bath, pre-ground and micronized under cryogenic conditions. Finally the microspheres were sifted at 125 µm and collected.

Example 4

2% Drug-Loaded Lipid Microparticles, Prepared by Co-Melting Technique Using Imwitor 900 as Lipid Matrix The lipid (Imwitor 900) was melted at 15° C. above its melting point. Afterwards the peptide (Antide) was incorporated into the molten lipid under stirring (the w/w drug-lipid ratio was 2:98). The lipid matrix was then cooled down in an ice-bath, pre-ground and micronized under cryogenic conditions. Finally the microspheres were sifted at 125 µm and collected.

Example 5

IFN-Beta Loaded LM, Prepared by Co-Melting Technique Using Imwitor 900 and Imwitor 312 (25:75) as Lipid Matrix Imwitor 900 and Imwitor 312 in powder form were mixed in the solid state and then co-melted in a water bath thermostated at 58° C.±2° C. IFN-beta liquid formulation (245 µg/mL) was added to the molten lipid kept at 58° C.±2° C. and allowed to dissolve within 20 minutes under gentle mixing. Then the mass spontaneously cooled at room temperature, manually reduced into coarse particles and stored at −80° C. Before milling the IFN-beta lipid formulation was kept at −80° C. for at least 12 hours. The grinding was performed using as operating conditions a rotor speed of 18000 rpm and a screen size of 0.5 mm. The ground material was stored at 4° C. Lipid Microparticles were characterized with their particle size distribution using Laser Diffractometer. The particle size analysis results are reported in Table 6.

Example 6

10% Drug-Loaded Lipid Microparticles, Prepared by Solvent-Stripping Technique Using Compritol E ATO as Lipid Matrix The peptide (Antide) and the lipid (Compritol E ATO) in a w/w ratio of 1:9 were solubilized at 85° C. in the organic solvent (Benzyl alcohol) under stirring. The solvent was evaporated under vacuum at 85° C. The lipid matrix was then cooled down to room temperature, pre-ground and micronized under cryogenic conditions. Finally the microspheres were sifted at 125 µm and collected.

Example 7

20% Drug-Loaded Lipid Microparticles, Prepared by Solvent-Stripping Technique Using Compritol E ATO as Lipid Matrix The peptide (Antide) and the lipid (Compritol E ATO) in a w/w ratio of 1:4 were solubilized at 85° C. in the organic solvent (Benzyl alcohol) under stirring. The solvent was evaporated under vacuum at 85° C. The lipid matrix was then cooled down to room temperature, pre-ground and micronized under cryogenic conditions. Finally the microspheres were sifted at 125 µm and collected.

Example 8

2% Drug-Loaded Lipid Microparticles, Prepared by Co-Melting Technique Using Compritol 888 ATO as Lipid Matrix The peptide (Antide) was incorporated into the molten lipid (Compritol 888 ATO) under stirring (the w/w drug-lipid ratio was 2:98). The lipid matrix was then cooled down in an ice-bath, pre-ground and micronized under cryogenic conditions. Finally the microspheres were sifted at 125 μm and collected.

Example 9

2% Drug-Loaded Lipid Microparticles, Prepared by Solvent-Stripping Technique Using Compritol 888 ATO as Lipid Matrix The peptide (Antide) and the lipid (Compritol 888 ATO) in a w/w ratio of 2:98 were solubilized at 85° C. in the organic solvent (Benzyl alcohol) under stirring. The solvent was evaporated under vacuum at 85° C. The lipid matrix was then cooled down to room temperature, pre-ground and micronized under cryogenic conditions. Finally the microspheres were sifted at 125 μm and collected.

Example 10

10% Drug-Loaded Lipid Microparticles, Prepared by Solvent-Stripping Technique Using Compritol 888 ATO as Lipid Matrix The peptide (Antide) and the lipid (Compritol 888 ATO) in a w/w ratio of 1:9 were solubilized at 85° C. in the organic solvent (Benzyl alcohol) under stirring. The solvent was evaporated under vacuum at 85° C. The lipid matrix was then cooled down to room temperature, pre-ground and micronized under cryogenic conditions. Finally the microspheres were sifted at 125 μm and collected. The characterization of the lipid microparticles prepared as described in the Examples 1-10 is reported below.

Example 11

Determination of Encapsulation Efficiency

Antide content in the lipid microparticles was determined by RP-HPLC: 50 mg of Antide-loaded lipid microparticles was first dissolved into 5 mL of acetone, shaken and sonicated for 2 minutes. 5 mL of distilled water were added to the acetone solution. The obtained mixture was sonicated for 2 minutes and subsequently centrifuged for 15 minutes at 8000 rpm.

The clear solution was injected into the HPLC column. The encapsulation efficiency values for some of the lipid microparticles formulations are presented hereinafter. The encapsulation efficiency was calculated as follows:

$$\text{encapsulation efficiency}\% = \frac{\text{drug content}(HPLC\text{ assay})}{\text{theoretical drug content}} \times 100$$

As described in the Table 2, it can be seen that satisfactory encapsulation efficiency was achieved with both drug incorporation methods and with both tested lipids.

Example 12

Determination of Peptide Stability within the Lipid Matrix lipid microparticles drug content was determined by RP-HPLC, as described in previous section, for two Antide-loaded Imwitor 900 formulations at t=0 and t=3 months, and the results are shown in Table 3.

Example 13

Physico-Chemical Characterization of the Microparticles

A complete physico-chemical characterization of the lipid microparticles was done evaluating their particle size distribution (determined by Laser Diffractometer analysis), surface analysis of the lipid matrices and NMR investigations. The weight yield of particles below 125 μm was also determined, as this fraction is suitable for s.c. administration.

The particle size and particle size distribution of Antide-loaded lipid microparticles formulation were evaluated by Laser Diffractometry (LD), using the Malvern's Laser Diffractometer. A small amount of lipid microparticles (about 40 mg) were dispersed in 50 μL of Tween 20 and then diluted in 5 mL deionized water, so to obtain an obscuration value between 5% and 30%. The sample was kept circulating within the dispersion unit during the analysis. At least three measurements were taken for each sample and the data were processed using the Fraunhofer diffraction model.

Figure 3:
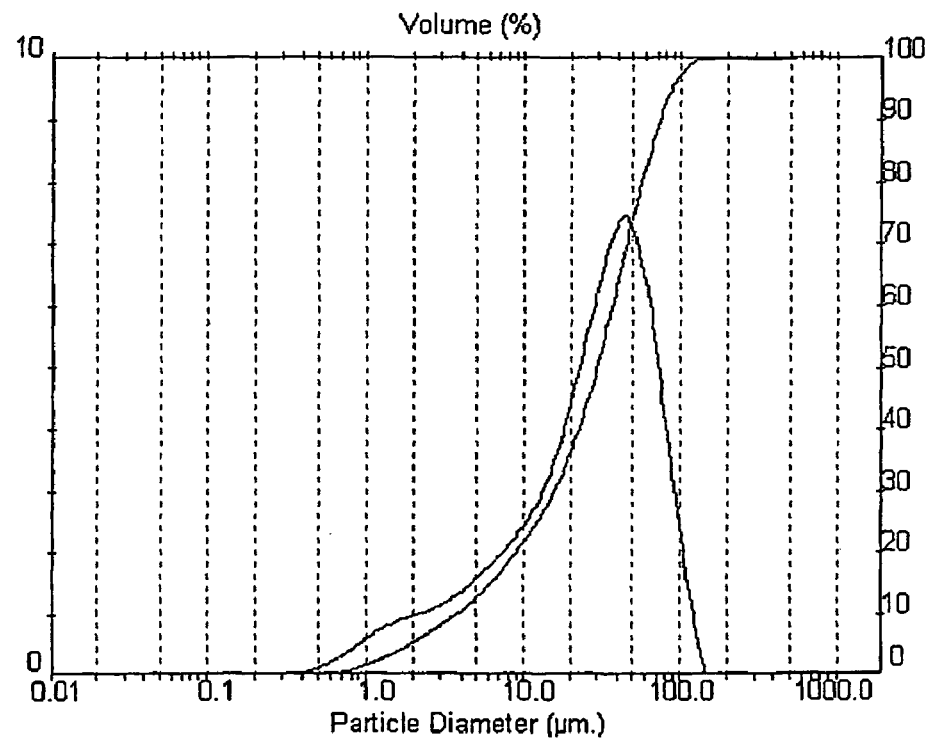
Figure 3:
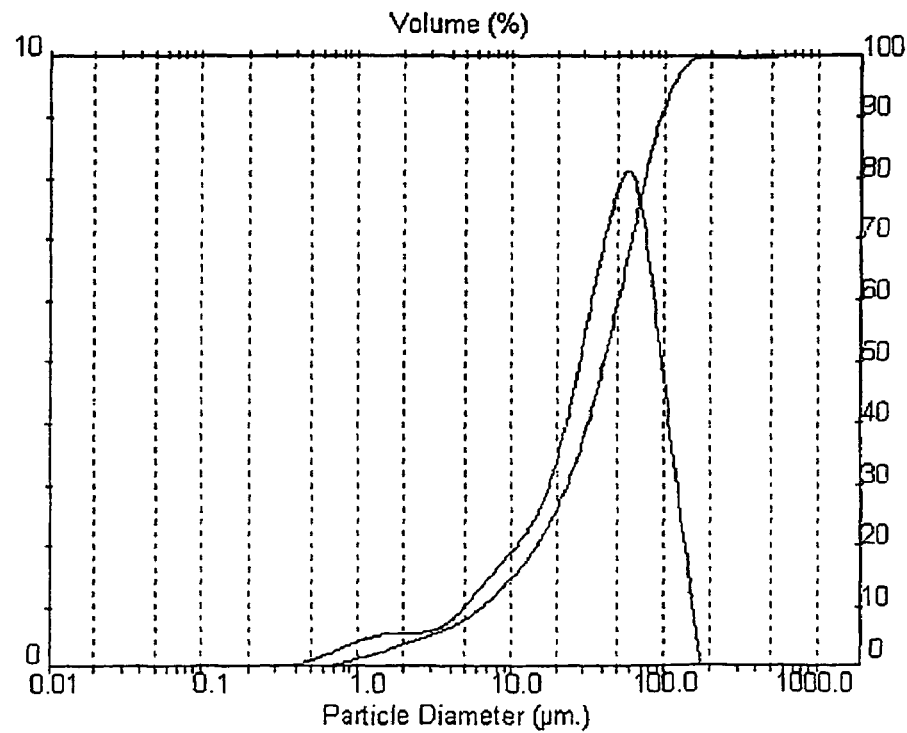

Examples of LD frequency curves and D (v, 0.1), D (v, 0.5) and D (v, 0.9) parameters, which define the size distribution of the population as follows:

- D (v, 0.1)=10% (in volume) of the particles have a size below this value;
- D (v, 0.5)=50% (in volume) of the particles have a size below this value;
- D (v, 0.9)=90% (in volume) of the particles have a size below this value; are shown in FIG. 3 and Table 4. As can be seen, both manufacturing methods gave rise to similar microparticles size distribution, mainly comprised between 1 and 125 μm.

Contact angle analysis of lipid matrices was carried out using a Kruss tensiometer (drop shape analysis system). The contact angle is the angle between a liquid droplet and a surface on which it spreads. It may be 0°, signifying complete wetting, or 180°, at which wetting is insignificant. The contact angle may also have any value between these limits.

Analysis was performed using water and preparing lipid matrices according to the manufacturing methods described. The comparison of the surface analysis results of the stripped and co-melted Antide-loaded lipid matrices is presented in Table 5.

Surprisingly, the two manufacturing methods gave very different θ° values, signifying that stripped matrices are quite less wettable by water (more lipophilic) than co-melted matrices (more hydrophilic), and likely indicating a very different structural arrangement of the lipid component in the matrix and in the particles. The presence of the drug did not modify significantly the surface characteristics of the lipid matrices. Therefore it can be expected that the matrix wettability properties are not affected by the incorporated drug.

Figure 4:
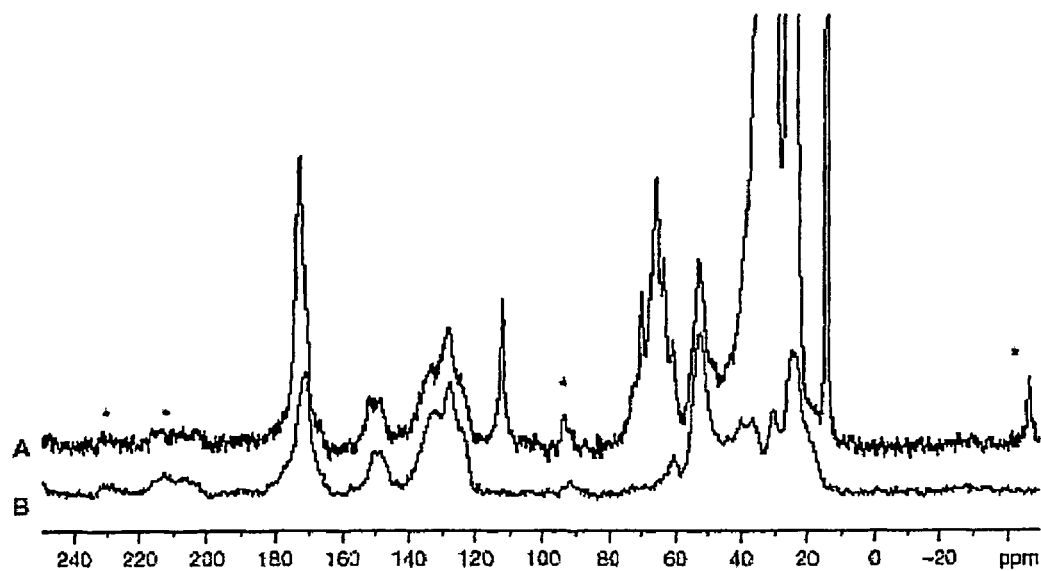
Figure 5:
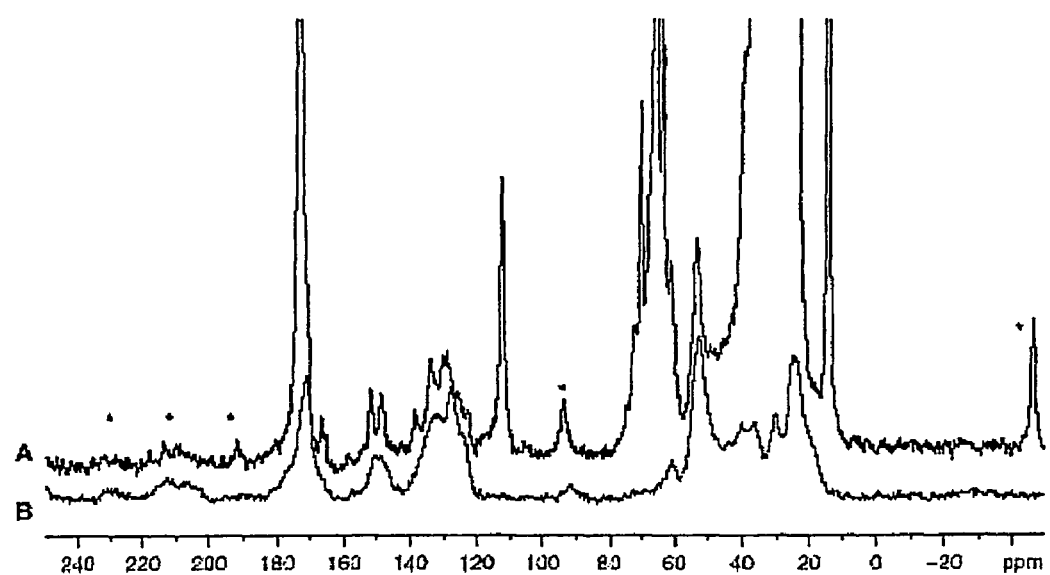

The lipid matrices were characterized by Solid State NMR analysis. $^{13}$C-NMR spectra of Antide conformation in bulk drug and lipid matrices prepared according to the aforementioned techniques are shown in FIGS. 4 and 5. Surprisingly, the broad peaks (on pyridine residues 3, 5, 6) observed in the bulk Antide are still present when the drug is incorporated by means of solvent-stripping method, while the same peaks are significantly sharper when the drug is loaded by co-melting technique. This demonstrates that the drug structure within the two matrices and the structural arrangement of the whole drug-lipid system depends on the manufacturing method used and on the composition. This could be ascribed to the presence of "microdomains" of drug molecules when co-melting is used. On the contrary a real "solid solution" is formed by solvent-stripping.

Example 14

In-Vitro Kinetic Release Pattern Assessment

Antide release from lipid microparticles was assessed using water (+$NaN_3$ 0.05% as preservative) or PBS (phosphate buffered saline) as release medium. The experiments were performed suspending about 40 mg of lipid microparticles in 20 mL of release medium. The suspensions were kept under stirring in a thermostated water bath at 37° C. 1 mL samples where withdrawn at different times, using a Teflon syringe and an Acrodisc 0.2 μm filter. The filtered lipid microparticles where returned back into the vessel, reintroducing an equivalent amount of release medium.

Figure 6:
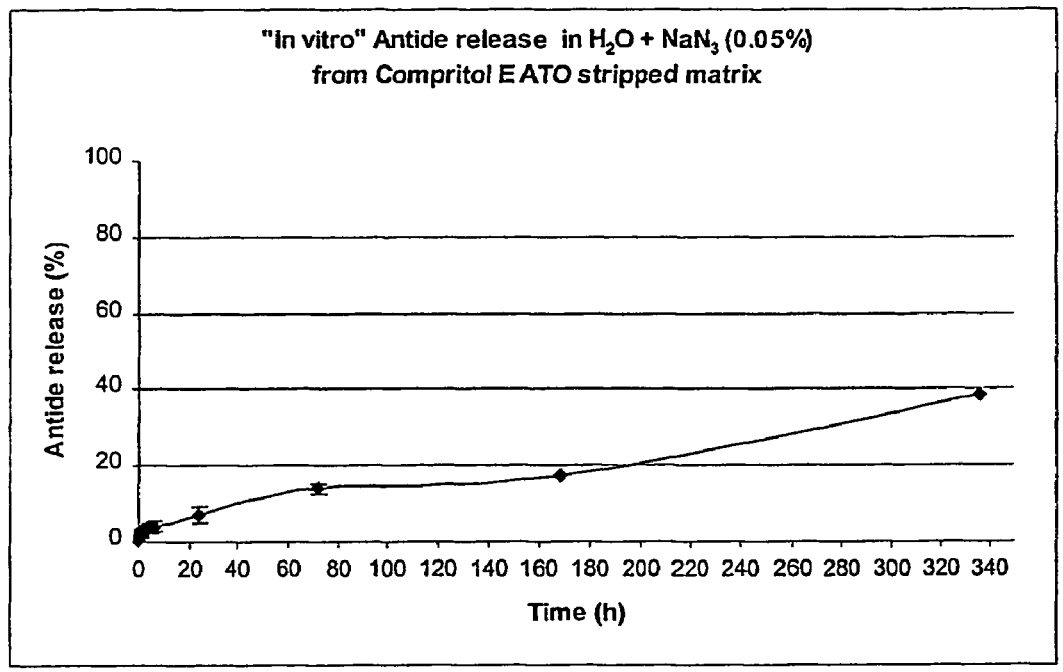
Figure 6:
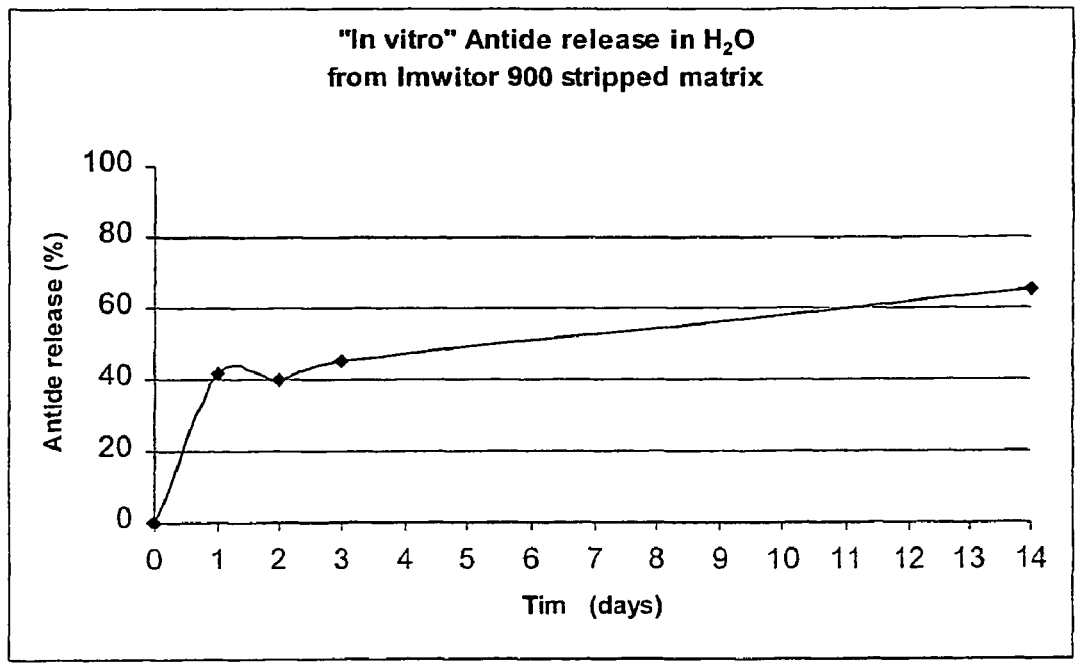
Figure 7:
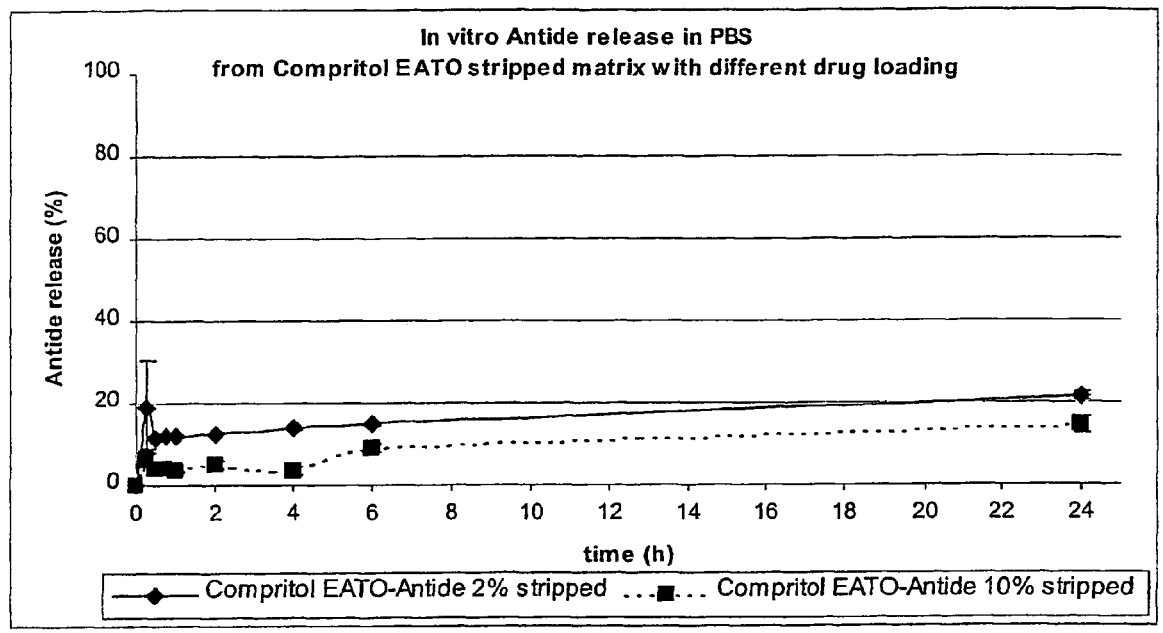

The release profiles of different lipid microparticles formulations are shown in FIG. 6. Unexpectedly, the "burst effect" was dramatically reduced with all these formulations. Noteworthy, with some formulations it was reduced down to less than 10% in 1 hour. Furthermore, for all the different lipids tested, the solvent-stripped matrices showed a lower release rate. This is explained by its lower surface wettability, as demonstrated by contact angle measurement, and by the presence of drug clusters in the co-melted microparticles, as shown by $^{13}CNMR$ spectra.

Noteworthy, in the case of Compritol E ATO matrices obtained by solvent-stripping method, a nearly "zero-order" release rate was achieved, this being a highly desirable profile in the case of long-term administration of anti-cancer drugs. This is a really surprising phenomenon, since a zero-order drug release kinetics is not usually obtainable by biodegradable microsphere systems.

Amazingly, this "quasi zero-order" release seems to be almost independent from drug loading, at least within the studied range 2-20% w/w. In fact, as it can be seen in FIG. 6, the fraction of Antide released, as well as its release kinetics, from the 10% loaded Compritol E ATO lipid microparticles within the first 24 hours, are comparable to those obtained with the corresponding 2% loaded matrix. This is quite unexpected, since it is commonly observed that drug burst from microparticle systems increases dramatically with drug loading.

Moreover, the drug release from Compritol E ATO matrices was surprisingly slower than the release kinetic from Imwitor 900 matrices. This can be ascribed to the different glyceride composition and physico-chemical properties of the lipid carrier.

Biological Results

Example 15

In Vitro Assay

Figure 2:
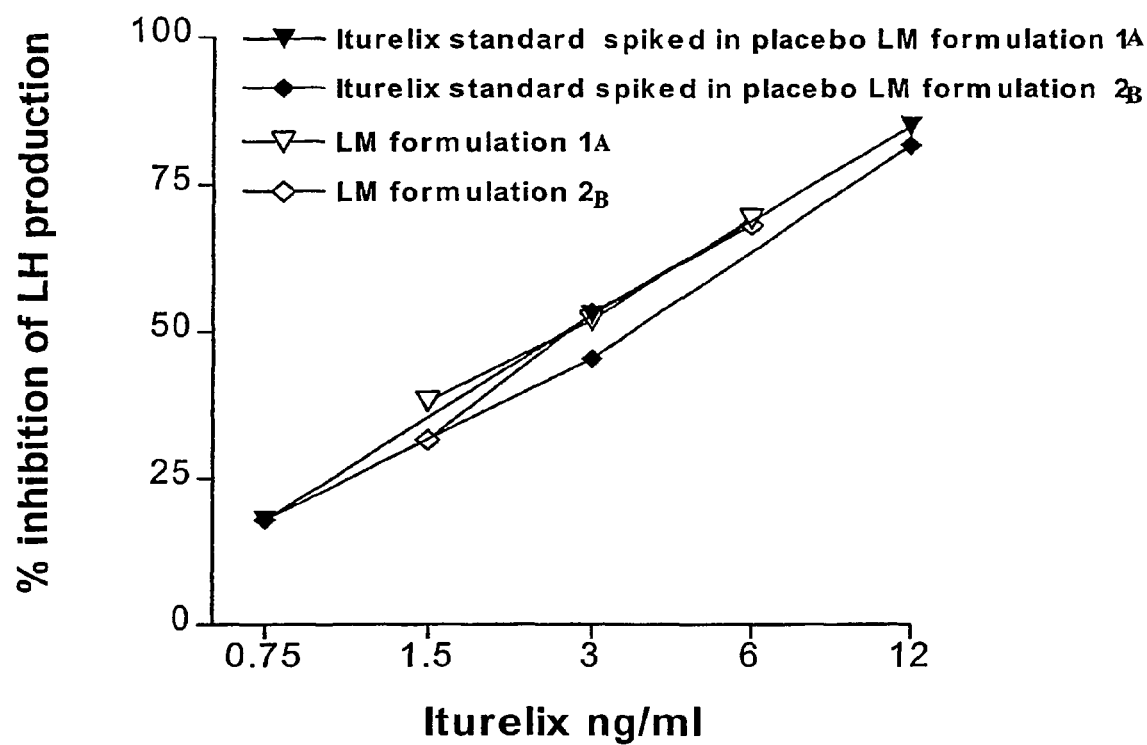
FIG. 2.

The results shown in FIG. 2 confirm that lipid microparticles preparation method did not cause any major modification of drug activity. This has been shown in the rat pituitary cell assay, carried out as described here below.

Primary culture of rat pituitary cells was established starting from enzymatic digestion of pituitary glands removed from female rats. Recovered cells were plated at $2.5 \times 10^5$/well in 24-well plates and cultured for 72 hours at 37° C. and 5% $CO_2$.

Wells were washed three times and then treated for 24 hours with 0.75, 1.5, 3, 6, and 12 ng/ml of two lipid microparticles-Antide formulations or in house reference standard Antide in triplicate. Wells for basal and maximum level of secreted LH received culture medium alone.

Then, after washing, samples and reference Antide dilutions were renewed and LHRH ($10^{-8}M$) was added in all the wells except to the basal wells that received equal volume of culture medium. Conditioned medium from each well was collected after 4 hours of incubation (37° C., 5% $CO_2$) and stored at −20° C. until assayed for LH content.

For the evaluation of secreted LH, a commercial RIA (Amersham Pharmacia Biotech) was used. Results were expressed as percentage inhibition of LH secretion by Antide.

By evaluating the in vitro inhibition of LH secretion by lipid microparticles on rat pituitary cells, it was demonstrated that the microparticles manufacturing process does not reduce the biological integrity of peptides. Results in FIG. 1 show that Antide bioactivity is maintained in the preparations tested.

Example 16

In Vivo Assay

Adult (63-70 days and about 300 g) Sprague Dawley male rats have been used in the study. The diet was available "ad libitum" to all the animals. The drinking water was also offered to the animals "ad libitum".

The test formulations containing lipid microparticles of Antide have been administered as one single subcutaneous dose of 0.6 mg (about 2 mg/kg) as Antide to each group of rats by subcutaneous route lipid microparticles of Antide have been administered in an approx. 5% glucose aqueous solution containing 0.05% Tween 20.

The microparticles contents in the vehicle was about 50 mg/ml. The volume of administration was 1 mL per rat.

The following experimental design was followed:

| | Group | | | | | | | | | |
|---|---|---|---|---|---|---|---|---|---|---|
| | 1 | 2 | 3 | 4 | 5 | 6 | 7 | 8 | 9 | 10 |
| Test article | Antide | Antide μ-particles Form. 1 | Antide μ-particles Form. 2 | Antide μ-particles Form. 3 | Antide μ-particles Form. 4 | Antide μ-particles Form. 1 | Antide μ-particles Form. 2 | Antide μ-particles Form. 3 | Antide μ-particles Form. 4 | Placebo μ-particles |

-continued

| | Group | | | | | | | | | |
|---|---|---|---|---|---|---|---|---|---|---|
| | 1 | 2 | 3 | 4 | 5 | 6 | 7 | 8 | 9 | 10 |
| Antide dose (mg) | 0.6 | 0.6 | 0.6 | 0.6 | 0.6 | 0.6 | 0.6 | 0.6 | 0.6 | 0 |
| No. rats/ group | 3 | 3 | 3 | 3 | 3 | 36 | 36 | 36 | 36 | 12 |
| Blood sampling | 0.5, 1, 2, 4, 8, 24 h | 0.5, 1, 2, 4, 8, 24 h | 0.5, 1, 2, 4, 8, 24 h | 0.5, 1, 2, 4, 8, 24 h | 0.5, 1, 2, 4, 8, 24 h | 0, 2, 3, 4, 5, 6, 8, 10, 12, 14, 21, 30 days | 0, 2, 3, 4, 5, 6, 8, 10, 12, 14, 21, 30 days | 0, 2, 3, 4, 5, 6, 8, 10, 12, 14, 21, 30 days | 0, 2, 3, 4, 5, 6, 8, 10, 12, 14, 21, 30 days | 1, 4, 8, 14, days |

Formulation 1: Antide (2% w/w)-Compritol E ATO (stripped)
Formulation 2: Antide (2% w/w)-Imwitor 900 (stripped)
Formulation 3: Antide (2% w/w)-Compritol E ATO (co-melted)
Formulation 4: Antide (2% w/w)-Imwitor 900 (co-melted)

The compounds have been administered to the animals which were fasted overnight prior to administration.

From animals of groups 1-5 about 0.5-1 ml of blood was drawn from a sublingual or tail vein at each sampling time up to 8 hours. At 24 hours (72 hours for group 1) the animals were anaesthetized with ether and killed by exsanguination from the abdominal aorta.

Animals of groups 5-8 were sampled by exsanguination from the abdominal aorta at the indicated sampling times.

Blood was collected in heparinized tubes and plasma separated by centrifugation (2500×g) at 4° C. Plasma obtained at sacrifice was divided into 3 aliquots of at least 1 ml.

The plasma concentrations of Antide was determined by an HPLC method with Mass Spectrometry detection (HPLC/MS/MS).

The pharmacodynamic marker testosterone was measured in all plasma samples taken at sacrifice.

Testosterone levels were determined using a RIA kit from Diagnostic Product Corporation (DPC).

Figure 8:
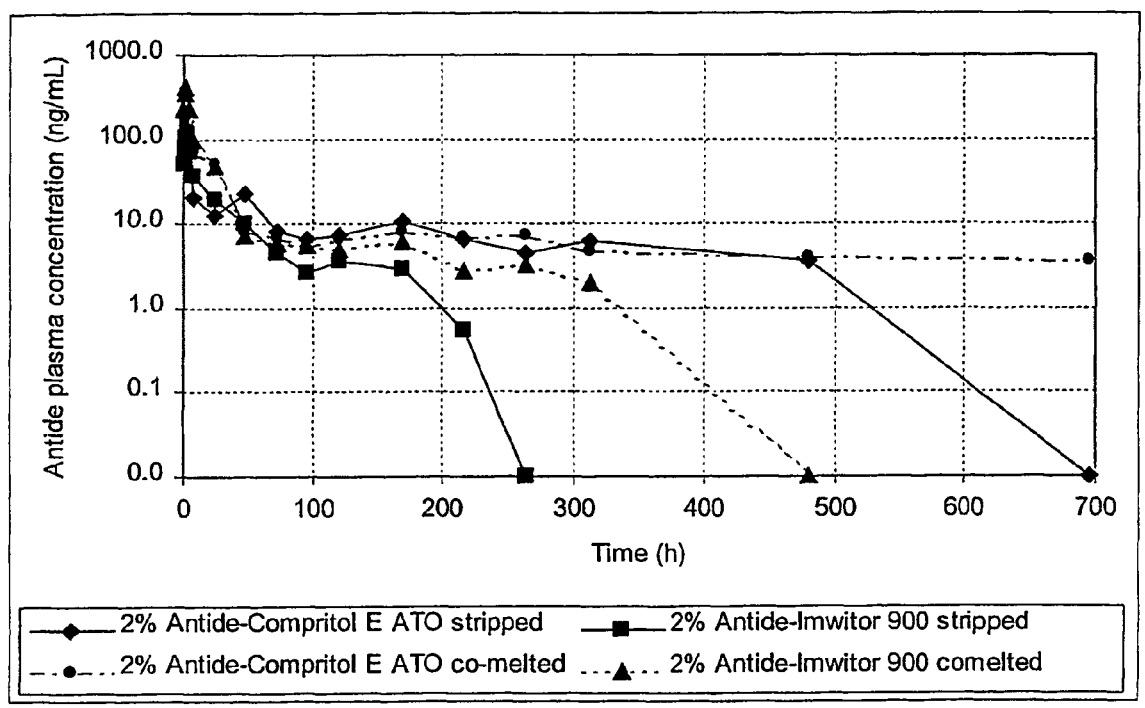
Figure 9:
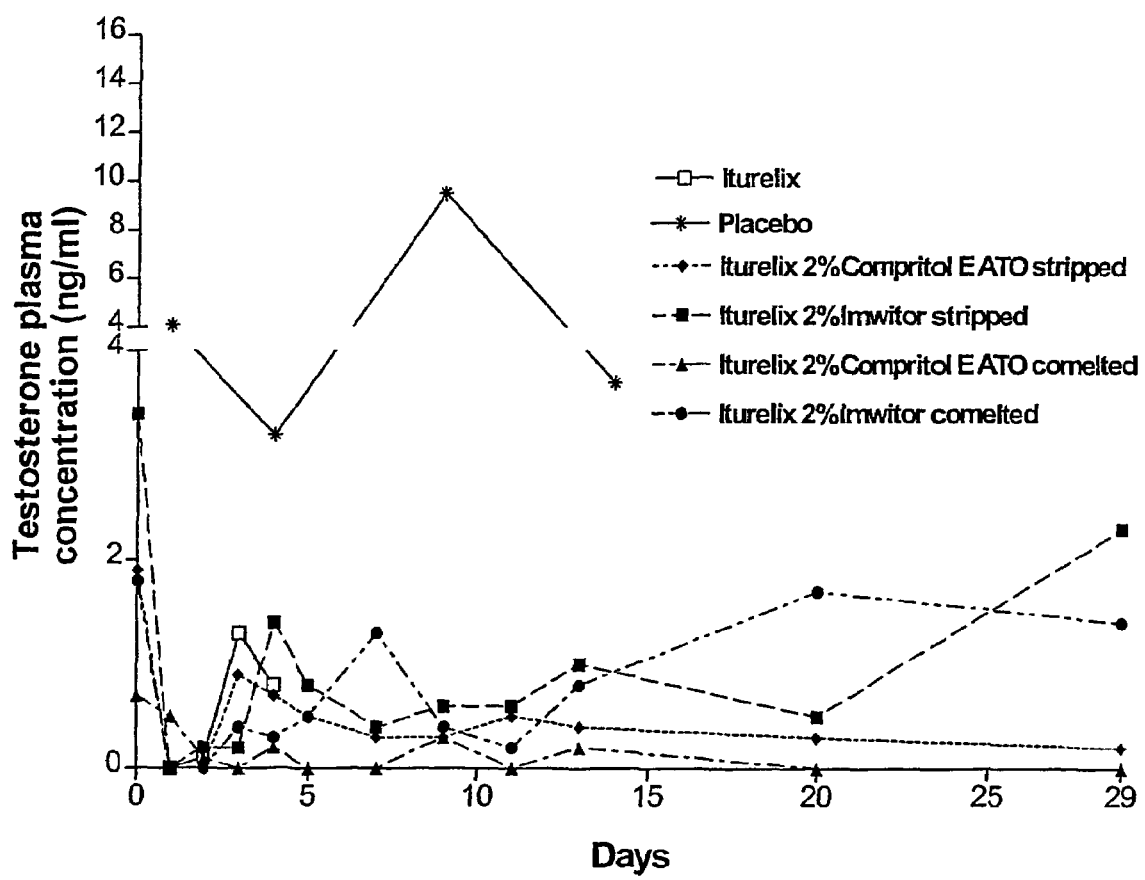
Figure 10:
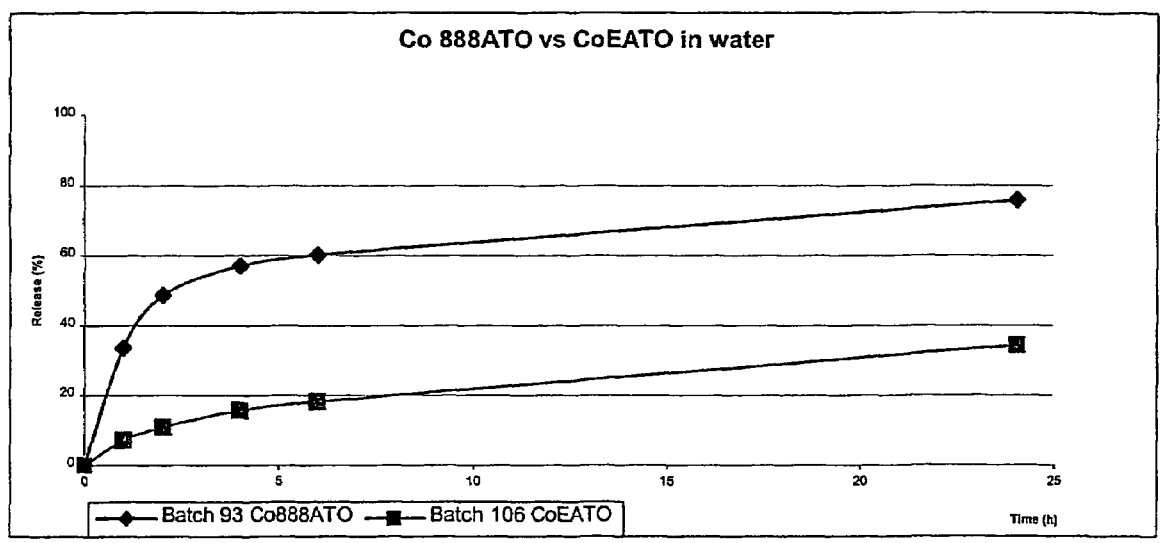

Antide and testosterone plasma levels were measured at different time points after administration and the results are shown in FIG. 8 and FIG. 9. Within the first 24-hours the plasma profile confirms the "burst reduction" observed in the in-vitro dissolution rate test. During 1 month observation both the drug PK profile and the PD effect on testosterone suppression were in agreement with the sustained release performance of the delivery system.

TABLE 1

Antide maximum loading in the pre-screened lipids, and monoglyceride content of the lipids.

| LIPIDS | | | Loading |
|---|---|---|---|
| Product | Chemical description | Monoglyceride content (%) | Antide loading (%) |
| Imwitor 312 | Monoglyceride of lauric acid | 95.30 | 2.2 |
| Imwitor 900* | Glyceryl mono-/di-stearate | 40-50 | 2.0 |
| Imwitor 928 | Glyceryl mono-/di-cocoate | 43.5 | $8.5 \times 10^{-1}$ |
| Geleol | Glyceryl mono-palmitate/stearate | 35 | 1.8 |
| Compritol E ATO | Glyceryl mono-/di-/tri-behenate | 80.40 | 1.7 |
| Compritol 888 ATO | Glyceryl behenate | 12-18 | $4.3 \times 10^{-1}$ |
| Compritol HD 5 ATO | Glyceryl/polyethylene glycol behenate | 1 | $1.7 \times 10^{-2}$ |
| Superpolystate | Polyethylene glycol stearate | <1 | $1.7 \times 10^{-1}$ |
| Precirol ATO 5 | Glyceryl mono-/di-/tri-palmitate/stearate | 8-17 | $5.9 \times 10^{-2}$ |
| Witepsol E 85 | Triglycerides of $C_{10}$-$C_{18}$ saturated fatty acids | <1 | $1.4 \times 10^{-2}$ - not soluble |
| Softisan 142 | Hydrogenated coco-glycerides | <1% | $1.7 \times 10^{-2}$ - not soluble |
| Gelot 64 | Glyceryl/polyethylene glycol palmitate/stearate | <1% | $5.8 \times 10^{-2}$ - not soluble |
| Monosteol | Palmitate/stearate of propylene glycol | <1% | $3.2 \times 10^{-2}$ - not soluble |
| Gelucire 44/14 | Defined blend of mono-/di-/tri-esters of lauric | <1% | $4.0 \times 10^{-2}$ - not soluble |

TABLE 1-continued

Antide maximum loading in the pre-screened lipids, and monoglyceride content of the lipids.

| Product | LIPIDS | | Loading |
|---|---|---|---|
| | Chemical description | Monoglyceride content (%) | Antide loading (%) |
| Gelucire 50/13 | acid with glycerol and polyethylene glycol Defined blend of mono-/di-/tri-esters of stearic acid with glycerol and polyethylene glycol | <1% | $3.0 \times 10^{-2}$ - not soluble |
| Cetil alcohol | Cetil alcohol | <1% | $3.7 \times 10^{-2}$ - not soluble |
| Tagat S | | <1% | $2.7 \times 10^{-2}$ - not soluble |

TABLE 2

Encapsulation efficiency of some lipid microparticles formulations obtained with Antide incorporation into lipid matrices using two different techniques (solvent stripping and co-melting).

| | Encapsulation efficiency (%) |
|---|---|
| 2% Antide-Compritol E ATO LM (stripped) | 88.5 |
| 2% Antide-Imwitor 900 LM (stripped) | 89.8 |
| 2% Antide-Compritol E ATO LM (co-melted) | 92.0 |
| 2% Antide-Imwitor 900 LM (co-melted) | 92.9 |

TABLE 3

Antide content (% w/w) in co-melted and stripped Imwitor matrices at t = 0 and after 3 months, determined by RP-HPLC.

| | Antide content (% w/w) | |
|---|---|---|
| | t = 0 | t = 3 months |
| Antide-Imwitor 900 LM co-melted | 1.7 | 1.8 |
| Antide-Imwitor 900 LM stripped | 1.7 | 1.7 |

TABLE 4

D (v, 0.1), D (v, 0.5) and D (v, 0.9) parameters of 2 lipid microparticles formulations.

| | D (v, 0.1) (μm) | D (v, 0.5) (μm) | D (v, 0.9) (μm) |
|---|---|---|---|
| 2% Antide-loaded Imwitor 900 co-melted matrix | 3.72 | 29.27 | 72.90 |
| 2% Antide-loaded Compritol E ATO stripped matrix | 6.38 | 40.65 | 94.09 |

TABLE 5

Comparison between the contact angle of Imwitor 900 matrices (both placebo and Antide-loaded) obtained by two different techniques: co-melting and stripping.

| | Contact angle (θ°) | |
|---|---|---|
| | Co-melted matrix | Stripped matrix |
| Placebo - Imwitor 900 matrix | 36.42° | 106.37° |
| 2% Antide loaded - Imwitor 900 matrix | 34.49° | 100.53° |

TABLE 6

Particle size distribution in IFN loaded Lipid Microparticles using co-melted technique:

| | % <125 μm | D(v, 0.5) (μm) | D(v, 0.9) (μm) |
|---|---|---|---|
| | 100 | 10.12 | 29.03 |
| | 100 | 8.78 | 22.23 |
| | 99.96 | 5.75 | 11.71 |
| avg | 99.99 | 8.22 | 20.99 |
| sd | 0.02 | 2.24 | 8.73 |

"avg" means average and "sd" means standard deviation

The invention claimed is:

1. Lipid microparticles comprising a drug and a lipid matrix characterized in that said drug is a peptide or a protein and said lipid matrix has a monoglyceride content which is at least 70% w/w, the percentage being based on the weight of the lipid matrix,
   wherein said lipid microparticles are prepared by preparing a drug-loaded matrix containing the drug and the lipid matrix, pre-reducing the size of the so-obtained drug-loaded lipid matrix by grinding, performing a cryogenic micronization, and milling the micronized drug-loaded lipid matrix particles,
   whereby the combination of the monoglyceride content and the process of cryogenic micronization is sufficient to inhibit a burst effect of the microparticles.

2. Lipid microparticles according to claim 1 characterized in that said monoglyceride content is comprised between 75 and 99% w/w, the percentage being based on the weight of the lipid matrix.

3. Lipid microparticles according to claim 1 characterized in that said drug is a protein.

4. Lipid microparticles according to claim 3 wherein said protein is IFN-beta.

5. Lipid microparticles according to claim 1 characterized in that said drug is a peptide.

6. Lipid microparticles according to claim 1 characterized in that said drug is a peptide selected from the group consisting of LHRH analogs.

7. Lipid microparticles according to claim 6 characterized in that said peptide is a decapeptide acting as LHRH antagonist.

8. Lipid microparticles according to claim 6 or 7 characterized in that said decapeptide is Antide, N—Ac-D-2-Nal, D-pClPhe, D-3-Pal, Ser, NicLys, D-NicLys, Leu, Ilys, Pro, D-Ala, $NH_2$.

9. Lipid microparticles according to claim 6 or 7 characterized in that said decapeptide is Cetrotide, N-acetyl-3-(2-naphthalenyl)-D-Ala-4-Cl-D-Phe-3-(3-pyridinyl)-D-Ala-L-Ser-L-Tyr-N5-(aminocarbonyl)-D-ornithyl-L-Leu-L-Arg-VPro.

10. Lipid microparticles according to claim 1 characterized in that said microparticles also comprise other pharmaceutically acceptable excipients.

11. Lipid microparticles according to claim 10 characterized in that the excipients are polymers with bioadhesive or absorption enhancing properties selected from the group consisting of acrylic polymers, medium chain fatty acids and polyethylene glycols.

12. Lipid microparticles according to claim 1 characterized in that said microparticles have an average diameter comprised in a range between 3 μm and 500 μm.

13. A pharmaceutical composition containing lipid microparticles according claim 1 and a pharmaceutically acceptable carrier, diluent or excipient thereof.

14. Process for the manufacture of lipid microparticles according to claim 1 comprising mixing the drug with the lipid co-solubilized in a solvent, eliminating the solvent, cooling the drug-loaded lipid matrix, pre-reducing the size of the so-obtained material by grinding, performing a cryogenic micronization and milling.

15. Process for the manufacture of lipid microparticles according to claim 1 comprising mixing said active compound with a molten lipid, cooling the drug-loaded lipid matrix, pre-reducing the size of the so-obtained material by grinding, performing a cryogenic micronization and milling.

16. The process according to claim 14 or 15, characterized in that it further comprises a sieving step after milling.

17. The process according to claim 14 or 15, characterized in that said cryogenic micronization step is performed at a temperature comprised of between −196° C. to 0° C.

18. The process according to claim 14 characterized in that said solvent is selected from the group consisting of water, ethanol, propanol, isopropanol, and benzyl alcohol or a mixture thereof.

19. The process according to claim 18 characterized in that said solvent is a mixture of ethanol and benzyl alcohol.

20. The process according to claim 18 characterized in that said solvent is benzyl alcohol.

21. The process according to claim 14 or 15 characterized in that cooling in said cryogenic micronization step is performed by insufflating liquid nitrogen.

22. Lipid microparticles obtained by a process according to claim 14.

23. Lipid microparticles consisting of a drug and a lipid matrix, wherein said drug is a peptide or a protein and said lipid matrix has a monoglyceride content which is at least 70% w/w, this percentage being based on the weight of the lipid matrix, and said microparticles are produced by cryogenic micronization.

24. The lipid microparticles according to claim 1 wherein said drug-loaded lipid matrix is prepared by mixing said drug with a lipid that is co-solubilized in a solvent and removing the solvent.

25. The lipid microparticles according to claim 1 wherein said drug-loaded lipid matrix is prepared by mixing said drug with a molten lipid and cooling the drug-loaded lipid matrix.

* * * * *